US00PP08842P

United States Patent [19]

Henny

[11] Patent Number: Plant 8,842

[45] Date of Patent: Jul. 19, 1994

[54] MANDEVILLA: RUBY STAR

[75] Inventor: Richard J. Henny, Tavares, Fla.

[73] Assignee: Gem Ornamentals Inc., Tavares, Fla.

[21] Appl. No.: 59,133

[22] Filed: May 7, 1993

[51] Int. Cl.[5] ..... A01H 5/00
[52] U.S. Cl. ..... Plt./54.1
[58] Field of Search ..... Plt. 54.1, 68.1

[56] References Cited

PUBLICATIONS

Bailey, L. H., et al., "Mandevilla" *Hortus Third*, MacMillan Pub. Co., Inc. N.Y. 1976 p. 711.

Graf, A. B., (Ed.), "Mandevilla" *Exotica* 1967 Roehrs Co., Rutherford, N.J., U.S.A., p. 1651.

Huxley, A., et al. (Eds.), "Mandevilla" *The New Royal Horticultural Society Dictionary of Gardening* 1992, vol. 3, p. 187.

*Primary Examiner*—James R. Feyrer
*Attorney, Agent, or Firm*—Merchant & Gould

[57] ABSTRACT

A new and distinct variety of Mandevilla characterized by large red flowers and shiny, dark evergreen leaves.

1 Drawing Sheet

BACKGROUND INFORMATION

The present invention relates to a new and distinct hybrid of Mandevilla that originated from self-pollination of Mandevilla × 'Alice Du Pont'. Mandevilla × 'Alice du Pont' is a hybrid from a cross of [*M. splendens* × (unknown species)] × *M. splendens* according to Bailey (see references). Pollinations were made by the inventor in a greenhouse at Gem Ornamentals Inc. in Tavares, Fla. in 1989. This new variety was selected for further evaluation because it had bright red flower color. The new variety has been reproduced by asexual propagation (cuttings). Each of the progeny, produced by asexual reproduction, exhibits identical characteristics to the original mother plant, establishing this hybrid as asexually reproducible and true to type.

This new variety is unlike any Mandevilla commercially available nor like any of those described by Graf or Bailey (see references) as evidenced by the following unique combinations of characteristics.

1. Red flowers—large funnelform to trumpet-shaped red flowers, darkening within 1–2 days after anthesis and remaining on the plant an additional 3–4 days.
2. Oblong-elliptic shaped, leathery, shiny dark green and evergreen leaves.
3. Corolla lobes irregularly obovate with acentric apex and minutely undulate margin.

DESCRIPTION OF THE DRAWING

This new variety of Mandevilla is illustrated by the accompanying photographic drawing.

DETAILED PLANT DESCRIPTION

Figure 1:
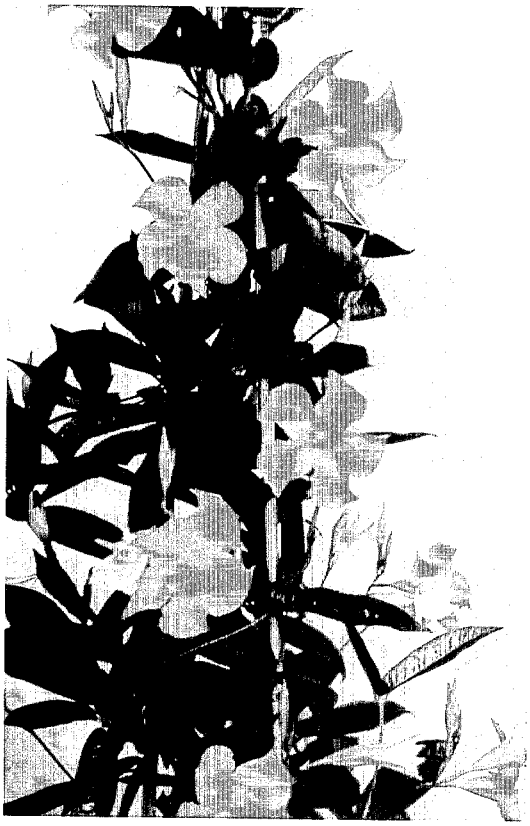
FIG. 1 is a photographic print in full color of a five-month old plant illustrating the red flowers, shiny leaves and vining growth habit.

The following is a detailed description of the new Mandevilla plant based on observations made at the nursery of Gem Ornamentals Inc. in Lake County, Tavares, Fla. where cuttings were rooted. The color determinations and comparisons are all based on The R.H.S. Colour Chart, published by The Royal Horticultural Society of England in association with Flower Council of Holland.

Overall size and growth habit:

*Size.*—The ultimate size of the new variety is unknown as no plant has reached full maturity. This new hybrid has grown between 1.0 to 1.5 m in 2 months under greenhouse conditions in the summer in Tavares, Fla.

*Growth habit.*—The growth habit is a vining liana, twining counter-clockwise, with evergreen, oblong to elliptic leaves and large funnelform to trumpet shaped red flowers borne in axillary clusters on new growth. a. Internode length of the hybrid is variable and similar to the parent plant. Internode lengths vary from 1 to 10 cm on the same vine with the shorter lengths near the base of the vine. This is due to such environmental factors as changes in light level due to weather or one vine shading another, variation in nutritional levels due to fertilization schedule, amount of water due to rain or irrigation frequency and temperature due to season of the year. The overall effect on the canopy is similar in the hybrid as with the parent plant. b. Plant growth of the hybrid and the parent plant is continuous throughout the year but faster in summer than in the winter. This is due to less total light in the winter as well as cooler temperatures. c. The ultimate plant size has not been determined but it should easily reach the 10 meter size (Graf, Exotica 3) if maintained in large enough containers under the proper cultural conditions. d. The growth rate of the hybrid is similar to the parent plant when propagated at the same time and grown under the same cultural conditions. e. Both the hybrid and its parent are very floriferous with bloom season extending from April through November in Tavares, Fla.

Stems: Stem sterete, olive-green, RHS Colour Chart Fan 3, Yellow-Green Group No. 144B; lighter towards the tips, RHS Colour Chart Fan 3, Yellow- Green Group No. 144C. Mature stem wood of the variety is RHS Colour Chart Fan 4 165A with areas of RHS Colour Chart Fan 4 199B. Stems densely velvety, tomentose, hairs erect; hairs colorless as seen with the naked eye. Nodul appendages fleshy, bi-and tridentate. Stems often tinged RHS Colour Chart Fan 2, Red-Purple Group 59B.

Foliage:

*Type.*—Evergreen, herbaceous.

*Arrangement.*—Opposite.

*Shape.*—Oblong to elliptic.

*Length.*—13.3 to 15.5 cm.

*Width.*—4.0 to 5.3 cm.

*Petiole.*—0.19 to 1.5 cm; channeled; tomentose.

*Margins.*—Repand and revolute.

*Apex.*—Acuminate.

*Base.*—Cordate.

*Texture.*—Leathery, minutely hairy.

*Venation.*—Pinnate, rugose.

*Color.*—Upper side of a mature leaf is glittering RHS Colour Chart Fan 3, Green Group 136A, midrib and veins are Colour Chart Fan 30 1, Green Group 143C. Underside is an opaque lighter green, RHS Colour Chart Fan 3, Green Group 138B.

Flowers:

*Arrangement.*—Flowers produced on lateral, axillary racemes producing flowers throughout the flower season (May through October in Tavares, Fla.).

*Peduncle.*—4.5 to 9.0 cm (axil to first bud scar).

*Raceme length.*—13.0 to 24.3 cm (base to highest bud).

*Number of buds.*—4 to 6.

*Number of open blooms.*—1 to 2.

*Pedicel.*—1.2 to 1.9 cm; twisted and densely minutely capilate.

*Bracts.*—4.0 to 5.5 mm width measured at base of pedicel. Bract tips all green. Bracts triangular; apex acute.

*Sepals.*—0.9 to 1.3 cm; minutely papillate on outside except at margins.

*Corolla tube.*—Straight; glaborous outside. Length 1.3 to 1.9. Diameter at base 0.4 cm.

*Corolla throat.*—Nearly conical. Length 4.0 to 4.2 cm. Opening width 2.0 to 2.2 cm.

*Corolla width.*—10.0 to 12.0 cm.

*Corolla lobes.*—Lobes are irregularly obovate. Apexes acentric and margins minutely undulate, subentire, very finely irregular. Length 5.0 to 5.4 cm; width 3.5 to 4.0 cm.

*Color.*—Bud: Rachis: Royal Horticultural Society Colour Chart Fan 3, Yellow-Green Group 144B. Pedicel: On bud and newly opening flower Royal Horticultural Society Colour Chart Fan 3, Yellow-Green Group 144B. Bractioles: Royal Horticultural Society Colour Chart Fan 3, Yellow-Green Group 144B. New bloom: Outside: Sepals: Royal Horticultural Society Colour Chart Fan 3, Yellow-Green Group 144A. Tips, margins and upper half are Royal Horticultural Society Colour Fan 2, Red-Purple Group 60A. Pedicels: beginning to be tinged at the base Royal Horticultural Society Colour Chart Fan 2, Red-Purple Group 60A. Corolla tube: The basal 3–4 mm are Royal Horticultural Society Colour Chart Fan 3, Yellow-Green Group 144B. The upper portion of the tube is Royal Horticultural Society Fan 1, Red Group 53B. Corolla throat: Main portion of the throat is Royal Horticultural Society Colour Chart Fan 1, Red Group 53B. The junction of the tube and throat appears lighter and is speckled with Royal Horticultural Society Colour Chart Fan 1, Red Group 53B over a background of Royal Horticultural Society Colour Chart Fan 4, Yellow-White Group 158C. Corolla lobes: The narrow side of the lobe is the same as the throat, Royal Horticultural Society Colour Chart Fan 1, Red Group 53B. On the wide side of the lobe there is an area along the midrib from the base to ⅔ way up and ¼ way from the midrib to the margin which is Royal Horticultural Society Colour Chart Fan 4, White Group 155C. The remainder of the lobe is Royal Horticultural Society Colour Chart Fan 1, Red Group 55B. Inside: Corolla lobe: The central base ⅓ portion of the lobe is Royal Horticultural Society Color Chart Fan 4, White Group 155C that then gradually becomes a region of Royal Horticultural Society Colour Chart Fan 1, Red Group 54A. Corolla throat: There is a band of Royal Horticultural Society Colour Chart Fan 3, Yellow-Green Group 151B ⅓ the length of the throat along the line of fusion of 2 petals. There is a 3 mm band extending from base to almost the top of the throat of Royal Horticultural Society Colour Chart Fan 4, Yellow-White 158B. There are five of such bands. Farther up, the throat at the junction of the throat to the corolla lobe is tinged with Royal Horticultural Society Color Chart Fan 2, Red Purple Group 63B. The area above the yellow band grading into the corolla is Royal Horticultural Society Color Chart Fan 1, Red Group 51B, most noticeable over the veins. Old bloom: [2 days after anthesis]: Outside: Corolla tube: The corolla tube is Royal Horticultural Society Color Chart Fan 1, Red Group 53A. Corolla throat: The corolla throat and the narrow portion of the corolla lobe are Royal Horticultural Society Colour Chart Fan 1, Red Group 46A. Corolla Lobe: The wider side of the corolla lobe is Royal Horticultural Society Colour Chart Fan 1, Red Group 53C along the midrib. Pedicel: The entire pedicel has become Royal Horticultural Society Colour Chart Fan 2, Red-Purple Group 60A. Inside: Corolla lobe: The color throughout is Royal Horticultural Society Colour Chart Fan 1, Red Group 46B. This color extends approximately 1 cm into the upper portion of the throat. The color is most prominent along the veins. Between the veins the color lightens to Royal Horticultural Society Colour Chart Fan 2, Red-Purple Group 63B. This results in a striping effect. The five bands along the fusion line of the petals is now Royal Horticultural Society Colour Chart Fan 4, White Group 155A and extend all the way to the base of the throat. The yellow bands now extend only about ¼ of the way up the throat and are now Royal Horticultural Society Colour Chart Fan 3, Yellow-Green Group 150D.

*Additional flower comments.*—1. The pedicel is twisted and minutely capillate. 2. The sepals on the outside are minutely papillate except at the margins. 3. The flowers are very faintly fragrant late in the afternoon. The fragrance is not distinguished from that of the parent plant.

Tubers: The tubers taken from a 1-year old plant were irregular in shape varying from cylindrical to globose with constrictions occurring at irregular intervals. The diameter was between 0.5 and 2.0 cm and tapered at the far end. Their color was R.H.S. Colour Chart Fan 4, Grey-Brown Group, No. 199A. The tubers of this variety have not been found to be distinguishable from the parent plant.

Fruit and seed: No fruit or seed have been observed on the new variety.

Cold hardiness: The new variety has withstood temperatures of 34° F. but is not frost tolerant.

Comparison of variety with parent Mandevilla × 'Alice du Pont':

Mandevilla × 'Alice du Pont'

*Leaf shape.*—Elliptic-oblong to ovate-oblong.

*Leaf length.*—10 cm to 13 cm, not as long as the new variety.

*Leaf width.*—4 cm to 6.5 cm, wider than the new variety.

*Petiole length.*—0.4 cm to 0.7 cm, shorter than the new variety.

*Stem and lower leaf surfaces.*—Beginning 7.5 cm to 12.5 cm from the growing tip, the lower leaf surfaces, midribs and/or stem show a pinkish-red pigmentation. Stems of the new variety are as previously described.

*Corolla width.*—9.5 cm to 11.5 cm, similar to the new variety.

*Tube and throat length.*—5 cm to 5.7 cm, slightly longer than the new variety.

*Flower color.*—Corolla opens pink, R.H.S. Colour Chart Fan 2, Red-Purple Group, No. 63C, but darkens to deep ink, R.H.S. Colour Chart Fan 2, Red-Purple, No. 63A. Throat color opens striated dark pink R.H.S. Colour Chart Fan 2, Red-Purple Group No. 64C and darkens to No. 63A. In addition, white, R.H.S. Colour Chart Fan 4, White Group No. 155B, is also visible at the base of the throat around the stamens on a mature flower. The new variety's throat is as previously described.

REFERENCES

Bailey, L. H. and E. Z. Bailey, 1976, *Hortus Third*, MacMillan, New York.

Graf, A. B., 1978, Tropica — Color Cyclopedia of Exotic Plants and Trees, Roehrs Co., East Rutherford, N.J.

Graf, A. B., (Ed.). 1967. "Mandevilla" *Exotica* 3. Roehrs Co., Rutherford, N.J., U.S.A. p. 1651.

I claim:

1. A new and distinct variety of Mandevilla substantially as shown and described, characterized by flowers that open pale pink and turn to red within two days and last an additional 3–4 days on the plant, and shiny green oblong to elliptically shaped leaves.

* * * * *

UNITED STATES PATENT AND TRADEMARK OFFICE

CERTIFICATE OF CORRECTION

PATENT NO. : Plant 8,842

DATED : July 19, 1994

INVENTOR(S) : Richard J. Henny

It is certified that error appears in the above-identified patent and that said Letters Patent is hereby corrected as shown below:

Column 1, line 41, insert --,-- after the word "Fla.".

Column 3, line 14, "0.19" should read --0.9--.

Column 3, line 22, "Fan 30I," should read --Fan 30,--.

Column 3, line 43, "glaborous" should read --glabrous--.

Column 5, line 1, "distinguished" should read --distinguishable--.

Column 6, line 7, "ink" should read --pink--.

Column 6, line 19, "MacMillan" should read --MacMillian--.

Signed and Sealed this

Eighth Day of November, 1994

*Attest:*

*Attesting Officer*

Bruce Lehman

BRUCE LEHMAN

*Commissioner of Patents and Trademarks*